(12) United States Patent
Grof et al.

(10) Patent No.: US 8,158,432 B2
(45) Date of Patent: Apr. 17, 2012

(54) METHOD AND SYSTEM FOR MARKING AND DETERMINING THE AUTHENTICITY OF LIQUID HYDROCARBONS

(75) Inventors: Yair Grof, Rehovot (IL); Moshe Soschin, Herzelia (IL); Uziel Ben-itzhak, Beir Oved (IL)

(73) Assignee: Atomic Energy Commission, State of Isreal, Yavne (IL)

( * ) Notice: Subject to any disclaimer, the term of this patent is extended or adjusted under 35 U.S.C. 154(b) by 1336 days.

(21) Appl. No.: 10/480,012

(22) PCT Filed: Jun. 3, 2002

(86) PCT No.: PCT/IL02/00431
§ 371 (c)(1),
(2), (4) Date: Mar. 8, 2004

(87) PCT Pub. No.: WO02/098199
PCT Pub. Date: Dec. 12, 2002

(65) Prior Publication Data
US 2004/0248307 A1    Dec. 9, 2004

Related U.S. Application Data

(60) Provisional application No. 60/295,910, filed on Jun. 4, 2001.

(51) Int. Cl.
*G01N 37/00*    (2006.01)
(52) U.S. Cl. ........... 436/56; 436/164; 436/172; 73/1.24; 73/861.07; 73/61.41

(58) Field of Classification Search .................. None
See application file for complete search history.

(56) References Cited

U.S. PATENT DOCUMENTS

| | | | |
|---|---|---|---|
| 4,153,418 A * | 5/1979 | Haas | 436/139 |
| 4,551,154 A | 11/1985 | Malcosky et al. | |
| 5,759,857 A * | 6/1998 | Goyal et al. | 436/3 |
| 5,831,151 A * | 11/1998 | Ondrus et al. | 73/61.41 |
| 5,841,016 A | 11/1998 | Hossain et al. | |
| 5,878,772 A * | 3/1999 | Belyea | 137/101.21 |
| 5,958,780 A * | 9/1999 | Asher et al. | 436/56 |
| 7,278,325 B2 * | 10/2007 | Fraser et al. | 73/861.07 |

OTHER PUBLICATIONS

Injuk et al. "Optimisation of total-reflection X-ray fluorescence for aerosol analysis" (Spectrochimica Acta Part B, 1955, v. 50, pp. 1787-1803).*

Narasimham in "Marker Technologies, the Answer to Fuel Adulteration: An Overview", SAE No. 2008-28-0123 http://www.saeindia.org/Control/download_file/12~22~2008~12~27~19~PM/053.pdf.*

(Continued)

Primary Examiner — Yelena G Gakh
(74) Attorney, Agent, or Firm — Fish & Richardson P.C.

(57) ABSTRACT

System (50) for marking a fluid by a marker, the fluid flowing from a source to a destination, the system including a sensor (58) for determining a value of a fluid property and a fluid flow controller (54) for admitting a selected amount of the marker to the fluid, wherein the selected amount is determined according to the fluid value and a predetermined concentration of the marker in the fluid in the destination.

19 Claims, 10 Drawing Sheets

OTHER PUBLICATIONS

"Using the world's best X-ray spectrometer to detect atomic vibrations—Frontlines—Riken Research", 2008 http://www.rikenresearch.riken.jp/eng/frontline/5446.*

Marsha Yon, "Coriolis Meters for Liquid Measurement", http://help.intellisitesuite.com/Hydrocarbon/papers/2260.pdf no date is available.*

Ron Jenkins, "X-Ray Techniques: Overview", Encyclopedia of Analytical Chemistry, R.A. Meyers (Ed.) (2000), pp. 13269-13288.

Wang et al., "The determination of silicon in airborne particulate matter by XRF and LA-UCP-MS", Journal of Radioanalytical and Nuclear Chemistry, vol. 242, No. 1 (1999).

Wilkinson et al., "A Review of Fuel Marker Programs to Identify and Control Fraud", (2008) SAE International.

Beckhoff et al., "The Discovery of X-Rays and Origin of X-Ray Fluorescence Analysis" Handbook of Practical X-Ray Fluorescence Analysis, Springer (2006) pp. 415.

* cited by examiner

METHOD AND SYSTEM FOR MARKING AND DETERMINING THE AUTHENTICITY OF LIQUID HYDROCARBONS

FIELD OF THE DISCLOSED TECHNIQUE

The disclosed technique relates to liquid hydrocarbons in general, and to methods and systems for marking liquid hydrocarbons, in particular.

BACKGROUND OF THE DISCLOSED TECHNIQUE

It is often desirable to identify the source of a liquid hydrocarbon, such as petroleum, naphtha, gasoline, diesel fuel, jet fuel, kerosene, lubricant, gas, liquefied gas and the like. Such a need arises for example, in case of suspected fraud, such as theft from pipes, transportation tankers and storage units, intentional or unintentional adulteration, dilution or mixing of fluid from different sources, oil spills or leaks from an uncertain origin to the earth or water, and so forth. The high values as well as evasion of taxation provide lucrative grounds that highly motivate rogue interference with the fluids. By marking the vulnerable liquid beforehand, it is possible to identify at a later stage whether the liquid remained genuinely intact or it was adulterated, diluted or otherwise interfered with.

Methods and systems for marking liquid hydrocarbons are known in the art. The terms "liquid hydrocarbon", "oil", "fuel", "fluid", and "petroleum", are synonymously applied herein in their broadest sense, to designate all similar fluids and liquids. The oil is generally marked by a substance which can be later detected, thereby identifying the source of the oil. For example, the substance can be an oil miscible liquid, which is added to the oil, and emits light at distinct wavelengths, when exposed to light or other radiation. A simple dyeing substance is mixed with the oil, thereby changing the color of the oil and allowing the oil to be identified according to the marked color. Alternatively, the marking substance can emit light at an invisible wavelength, wherein the oil is identified by measuring the emitted wavelength by an optical detector. According to other methods, the fuel is marked with an organic compound whose presence is later detected by a spectrometer or a chromatograph. In general, the marker has to satisfy certain criteria pertinent to the specific marked fluid. For example—cost, ease of detection, stability, solubility and compatibility with the fluid (such as flammability with the marked fuel in engines), inertness to air, water and normal soil components, corrosiveness, volatility, and toxicity.

U.S. Pat. No. 5,598,451 issued to Ohno et al., and entitled "Apparatus for Measuring the Sulfur Component Contained in Oil", is directed to an apparatus for detecting the sulfur component contained in an oil. The apparatus includes a high voltage power supply, an X-ray tube, a filter, a sample cell, an X-ray window, an X-ray detector and a measurement circuit. The high voltage power supply is coupled to the X-ray tube for generating X-rays. The measurement circuit is coupled to the X-ray detector. The filter is located between the X-ray tube and the sample window. The sample cell is located between a sample inlet and a sample outlet and the sample flows through the sample cell. The X-ray window is located in front of the sample cell. The X-ray tube, the filter, the sample window and the X-ray detector are located in such position, that X-rays emitted by the X-ray tube toward the X-ray window and reflected by the X-ray window, strike the X-ray detector.

The X-ray tube includes a target made of Titanium. The X-ray window is made of Beryllium. The sample contains sulfur. X-rays, generated by the X-ray tube and filtered by the filter, strike the sample cell through the sample window. Fluorescent X-rays, which are radiated from the sulfur contained in the sample, strike the X-ray detector. The measurement circuit determines the concentration in weight of the sulfur contained in the sample, by measuring the detected X-ray intensity of the K-shell characteristic X-rays of the sulfur.

U.S. Pat. No. 6,214,624 issued to Barker et al., and entitled "Use of Perfluorocarbons as Tracers in Chemical Compositions", is directed to a method for marking a liquid medium by a perfluorocarbon tracer. The perfluorocarbon tracer is dissolved, admixed, dispersed or emulsified in the liquid medium. At the detections stage, a sample of the liquid medium is collected on activated carbon, desorbed and passed over a strong oxidizing catalyst, such as a 10-25% $V_2O_2/Al_2O_3$ catalyst, thereby combusting non-perfluorocabonated material. The water is removed from the combusted sample, by employing a semi-permeable membrane, and the combusted sample is introduced into a gas chromatograph equipped with a standard electron capture detector interfaced and a recorder.

U.S. Pat. No. 6,312,958 issued to Meyer et al., and entitled "Method for Marking Liquids with at Least Two Marker Substances and Method for Detecting Them", is directed to marking liquids with at least two markers, such that the fraudulent liquid is detected, even if the fraudulent liquid is mischievously marked with markers similar to the original ones. Meyer teaches the use of at least two markers having overlapping absorption ranges, which makes possible to use a large number of markers within a given wavelength range. The compounds used by others to misrepresent the original liquid, have to have not just absorption maxima similar to the original markers, but also characteristics similar to the original markers in the rest of the absorption range. Each fraudulent marker can have only one relatively narrow absorption maximum which corresponds with that of one of the original markers. If light sources are used to emit only in the regions of the absorption maxima, then similar fluorescence spectra are likely to result in both cases. However, if light sources are used which emit at wavelengths which the fraudulent markers have no absorption, but at which the original markers have overlapping absorption ranges, then fluorescent light emitted by these markers is detected in the case of original markers, but not in the case of fraudulent markers.

U.S. Pat. No. 5,980,593 issued to Friswell et al., and entitled "Silent Fluorescent Petroleum Markers", is directed to a method to mark a liquid product by a group of markers and a method to identify a liquid product. The marker is a compound which is synthesized by esterification of an appropriately selected linear or branched $C_1$-$C_{18}$ alkyl carboxylic acid. According to the patent, $C_5$-$C_{10}$ alkyl carboxylic acids are employed to mark fuels, because of reduced interference from background fluorescence. The concentration of the marker in the liquid petroleum product is generally at least about 0.25 ppm.

Extraction of the marker from the tagged petroleum product for detection purposes can be performed with a solution composed of 5-60 volume percent of a water miscible, petroleum-immiscible bridging solvent, water, a mineral alkaline source, such as KOH, and/or an alkyl or alkoxy amine. As a field test, a suitable volume of the aqueous extractant mixture is mixed with a suitable volume of the liquid petroleum which is to be tested. If the marker is present in the petroleum product, it will be extracted by the aqueous layer and caused to fluoresce by reaction with the extraction mixture. A hand held ultraviolet light source is used to qualitatively detect the marker. According to this method, it is possible to determine marker levels to within about 5%. As an example, a fuel was tagged with 3 ppm of the marker dissolved in isooctane. The marker was extracted and tested under an ultraviolet lamp, thus providing a blue fluorescent glow, which indicated the presence of the marker.

SUMMARY OF THE DISCLOSED TECHNIQUE

It is an object of the disclosed technique to provide a novel method and system for marking a fluid and determining the authenticity of a fluid.

In accordance with the disclosed technique, there is thus provided a system for marking a fluid by a marker, the fluid flowing from a source to a destination. The system includes a sensor for determining a fluid value of a fluid property of the fluid and a fluid flow controller for admitting a selected amount of the marker to the fluid. The selected amount is determined according to the fluid value and a predetermined concentration of the marker in the fluid in the destination.

In accordance with another aspect of the disclosed technique, there is thus provided a method for marking a fluid by a marker, the fluid flowing from a source to a destination. The method includes the procedures of measuring a property of the fluid, determining the amount of the marker to be added to the fluid, according to the measured property and adding the determined amount to the fluid, thereby marking the fluid.

In accordance with a further aspect of the disclosed technique, there is thus provided a method for determining the authenticity of a fluid. The method includes the procedures of comparing the concentration of a primary marker in the fluid with a predetermined concentration and determining a first authenticity of the fluid, according to the outcome of the comparison. The method further includes the procedures of increasing the concentration of a secondary marker in the fluid, when the first authenticity is positive, determining the presence of the secondary marker in the fluid and determining a second authenticity of the fluid, according to the outcome of the procedure for determining the presence of the secondary marker.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1:
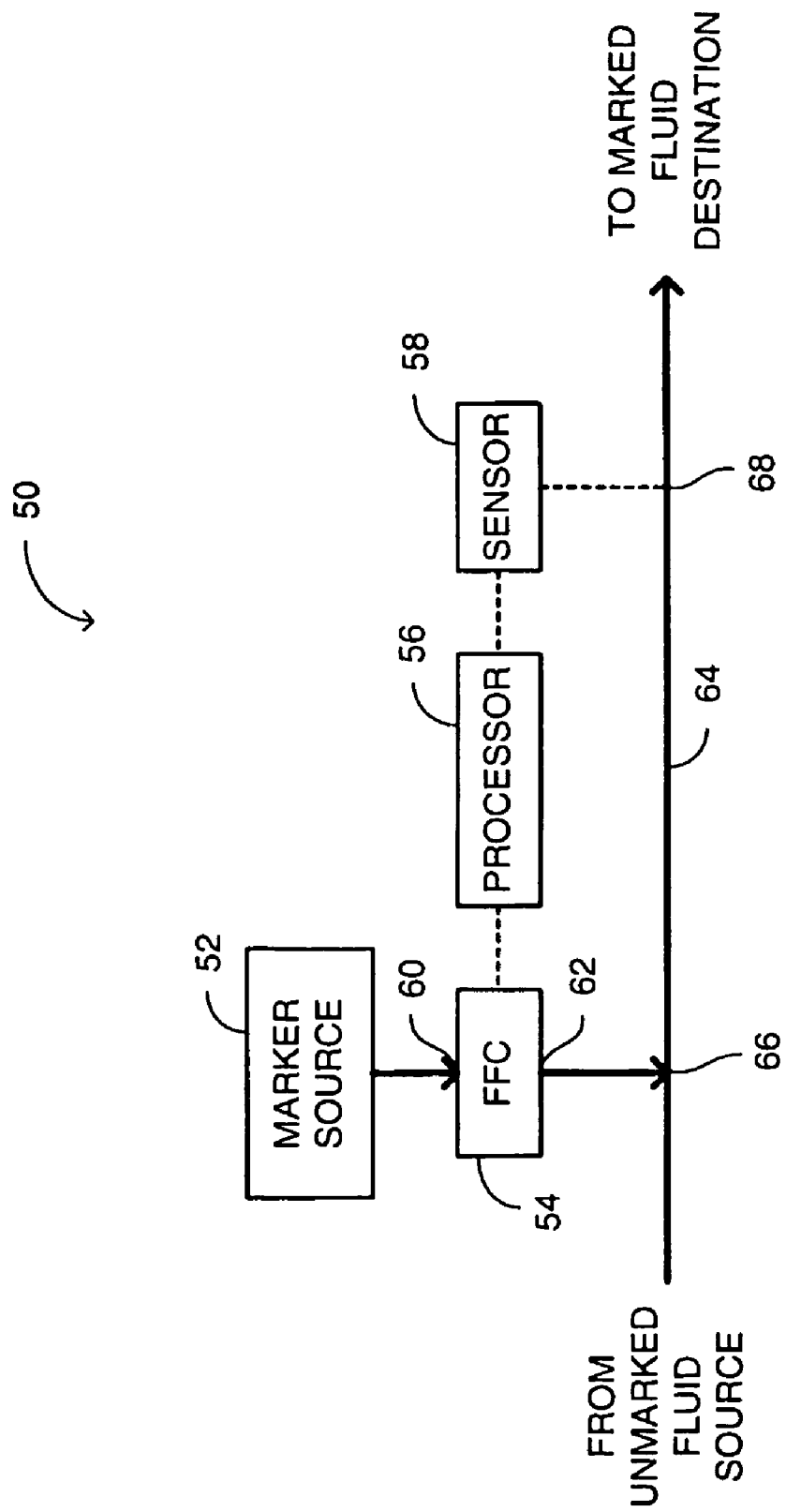
FIG. 1 is a schematic illustration of a fluid marking system, constructed and operative in accordance with an embodiment of the disclosed technique.

In its broadest aspects, the disclosed technique provides a system and a method for controlling the amount of a marker added to an unmarked fluid, such that a selected marker concentration in the fluid is obtained. Furthermore, a combination of a plurality of markers can be added to the unmarked fluid, each at a selected concentration.

The term "fluid" herein below, refers to any liquid hydrocarbon, including petroleum products either refined or unrefined, such as crude oil, naphtha, gasoline, diesel fuel, jet fuel, kerosene, propane, lubricant (e.g., engine oil), hydraulic fluid, natural gas (either in gaseous or liquefied form), and the like. In the drawings described herein below, solid lines designate physical fluid flow lines, whereas broken lines designate communication lines, signal control lines and measurement signal lines, either wired or wireless.

Reference is now made to FIG. 1, which is a schematic illustration of a fluid marking system, generally referenced 50, constructed and operative in accordance with an embodiment of the disclosed technique. Fluid marking system 50 includes a marker source 52, a fluid flow controller (FFC) 54, a processor 56 and a sensor 58. Fluid flow controller 54 can be either a pump or a valve. However, in the description herein below, fluid flow controller 54 is designated to be a pump. Fluid flow controller 54 includes an inlet 60 and an outlet 62.

Marker source 52 contains a marker (not shown) which is stable, miscible in and compatible with the fluid which is to be marked. For example the marker satisfies certain requirements such as being environmental-friendly (i.e., not harmful to the air, water, soil components, living organisms, and the like), non-corrosive, non-volatile, non-toxic, compatible with the machinery which operates on the fluid (e.g., engine, fuel cell, hydraulic system which uses the fluid, brake system, automatic transmission and so forth).

According to one example the marker can be based on an alkane, whose formula is $C_nH_{2n+2}$, where n=1, 2, 3 . . . . At least one hydrogen atom is substituted by an element which can be detected by an X-ray fluorescence analyzer (XRF). The resultant compound is having general formula $C_nH_{2n+2-m}X_m$, where n=1, 2, 3 . . . , and m=1, 2, 3 . . . "X" is any element which can be detected by an X-ray fluorescence analyzer (XRF). Simple example for this element is lithium (Li), an alkali metal, which forms one covalent bond with a carbon atom.

According to another example the marker can be a halogenic compound, such as an alkyl halide having the general formula $C_nH_{2n+2-m}X_m$, where n=1, 2, 3 . . . , m=1, 2, 3 . . . "X" is a halogen such as fluorine (F), chlorine (Cl), bromine (Br), and iodine (I). An example of such an alkyl halide is tetrabromoethane having the molecular formula $C_2H_2Br_4$ and having the Kekulé formula

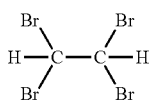

Following are the chemical names and molecular formulae of some of further examples of the marker in the form of alkyl halide: 1,1,2,2 tetrachloroethane (i.e., $C_2H_2Cl_4$), 1,1,2 trichloroethane (i.e., $C_2H_3Cl_3$), pentachloroethane (i.e., $C_2HCl_5$), hexachloroethane (i.e., $C_2Cl_6$), 1,2,4 trichlorobenzene (i.e., $C_6H_9Cl_3$), 1,2,4,5 tetrachlorobenzene (i.e., $C_6H_8Cl_4$), ethyliodide (i.e., $C_2H_5I$), ethylbromide (i.e., $C_2H_5Br$), dichloro 1,2 dibromoethane (i.e., $C_2H_2Cl_2Br_2$), dichlorotribromoethane (i.e., $C_2HCl_2Br_3$), difluoro 1 chloroethane (i.e., $C_2H_3F_2Cl$), difluoro 1,2 dibromoethane (i.e., $C_2H_2F_2Br_2$), trifluoro 1,2,2 dibromoethane (i.e., $C_2HF_3Br_2$), tribromopropane (i.e., $C_5H_7Br_3$), dibromobenzene (i.e., $C_6H_{10}Br_2$), dibromoethane (i.e., $C_2H_4Br_4$), n-propylbromide (i.e., $C_3H_7Br$), parabromofluorobenzene (i.e., $C_6H_{10}FBr$) having the Kekule formula

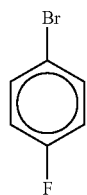

butylbromide (i.e., $C_4H_9Br$) and octylbromide (i.e., $C_8H_{15}Br$).

For marking fluids in gaseous state, gaseous markers can be used. For example, methane (i.e., $CH_4$) is in gaseous state under normal conditions. Halogens can substitute the hydrogen atoms, according to the formula $CH_{4-m}X_m$ where m=1, 2, 3, 4. "X" is a halogen such as fluorine (F), chlorine (Cl), bromine (Br), and iodine (I) or an alkali metal such as lithium (Li). Such markers can be for example methylbromide (i.e., $CH_3Br$), methyliodide (i.e., $CH_3I$), bromochloromethane (i.e., $CH_2BrCl$), and the like.

According to another example, the marker can be an organometallic or a halogenic compound in which at least one metallic element or at least one halogen, bonds with at least one carbon atom of an alkene (olefine), having the general formula $C_nH_{2n-m}X_m$, where n=1, 2, 3 . . . , m=1, 2, 3 . . . "X" is either an alkali metal or a halogen. An example of such a compound is bromoethylene having the molecular formula $C_2H_3Br$.

According to a further example the marker can be any of the above mentioned compounds wherein silicon (Si), germanium (Ge), and the like, substitutes an atom of carbon. For example, diethyl silane (i.e., $C_4H_{12}Si$) is such a compound. It will be noted that silicon is detectable by X-ray fluorescence analyzer and no substitutions for hydrogen atoms are necessary. Accordingly, "X" elements do not need to appear in the compound, if the silicon, germanium and the like serve as the marking element detectable by the X-ray fluorescence analyzer. For alkanes, the general formula of the compound is $C_{n-m}H_{2n+2}Y_m$, where n=1, 2, 3 . . . , m=1, 2, 3 . . . , m<n and where "Y" designates the silicon, germanium and the like. For alkenes (olefines), the general formula of the compound is $C_{n-m}H_{2n}Y_m$, where n=1, 2, 3 . . . , m=1, 2, 3 . . . and where "Y" designates the silicon, germanium and the like.

The marker can be in fluid form (i.e., gas or liquid) or solid (e.g., powder, miscible body, and the like) and either radioactive or non-radioactive. Marker source 52 can contain different types of markers.

Fluid flow controller 54 can be a pump of a type known in the art, such as a pulsating pump which delivers a predetermined volume of a fluid at each stroke of a piston. Fluid flow controller 54 can be either a constant displacement pump or a variable displacement pump. Sensor 58 can be a temperature sensor, flowmeter, viscometer, density meter, or any combination thereof. Sensor 58 can include an optical device, a device for measuring dielectric constant, spectrometer, X-ray fluorescence (XRF) analyzer, gas chromatograph, radiation detector, ultrasound detector, and the like, or a combination of the above.

Processor 56 is a digital signal processor (DSP), system on chip (SOC), and the like. Processor 56 is coupled with fluid flow controller 54 and with sensor 58. Marker source 52 is coupled with inlet 60. Outlet 62 is coupled with a conduit 64 at a marker injection point 66. A fluid flows in conduit 64 from an unmarked fluid source (not shown) to a marked fluid destination (not shown).

The fluid flows in conduit 64 from the unmarked fluid source to the marked fluid destination, either by gravity or by the action of a pump (not shown). Sensor 58 is coupled with conduit 64 at a measurement point 68. Measurement point 68 can be located either upstream of marker injection point 66 or downstream thereof.

"Sensor 58 determines the value of at least one property or parameter of the fluid which flows within conduit 64. The measured property includes at least the fluid flow rate (e.g., sensor 58 is a flowmeter). The measured property may also be the temperature, viscosity, or density. The property or parameter is measured in order to determine the amount of the marker to be added to the fluid, such that the concentration of the marker in the marked fluid will be controlled in a substantially accurate manner. Thus, sensor 58 measures the value of the property or parameter of the fluid which flows within conduit 64. Sensor 58 sends a signal respective of the measured property or parameter to processor 56. Processor 56 determines the amount of the marker which is to be added to the fluid, by processing the signal received from sensor 58, such that when all the fluid transfers from the unmarked fluid source to the marked fluid destination, the marker concentration at the marked fluid destination matches a selected value. Alternatively, processor 56 determines the amount of the marker, in order to maintain the marker concentration in the flowing fluid, at a selected value during the entire period of fluid flow from the unmarked fluid source to the marked fluid destination. In either case, processor 56 determines the amount of the marker, by employing a look-up table, an algorithm, a database (not shown), and the like."

Processor 56 controls the operation of fluid flow controller 54, such that fluid flow controller 54 delivers the determined amount of marker to the flowing fluid. For example, if fluid flow controller 54 is a constant displacement pump, then processor 56 provides a signal to fluid flow controller 54, to operate for a selected period of time corresponding to the determined amount. If fluid flow controller 54 is a variable displacement pump, then processor 56 provides a signal to fluid flow controller 54, such that fluid flow controller 54 operates at a rate to deliver the determined amount of the marker to the flowing fluid, within a given period of time.

Thus, fluid flow controller 54 delivers the amount of marker as determined by processor 56, from marker source 52 to the fluid at marker injection point 66. It is noted that the marker concentration in the flowing fluid depends on at least one property of the flowing fluid at any given time. Therefore, in order to maintain this marker concentration at a constant selected level, it is necessary to continuously measure this property and operate fluid flow controller 54 accordingly.

"For example, in order to maintain the marker concentration in a flowing fluid at a constant value, a greater amount of marker has to be added to the fluid when the flow rate of the fluid within conduit 64 is greater and a lower amount has to be added when the flow rate of the fluid is lower. Thus, if sensor 58 is in form of a flowmeter, it measures the flow rate of the fluid which flows in conduit 64 and sends a signal respective of this signal to processor 56. The mass of the fluid flowing in a specific volume within a specific period (e.g., in conduit 64) or stored in a specific volume (e.g., a container) depends on the temperature, viscosity, or density of the fluid, and therefore the amount of the marker which is to be added to the fluid, has to be adjusted accordingly."

In case fluid flow controller 54 is a pump, each entry of a predetermined marker concentration includes a pump operation time for each fluid flow rate. For example, the entry of the predetermined marker concentration corresponds to pump operation time of 10 seconds per minute, for fluid flow rate of 10,000 liters per hour (l/hr). In this case, fluid flow controller 54 delivers, say, 55 milliliters (ml) of the marker when operating for 10 seconds. Thus, if sensor 58 measures a flow rate of 12,000 l/hr of the flowing fluid at measurement point 68, then processor 56 directs fluid flow controller 54 to operate for 12 seconds, thereby adding 66 ml of the marker to the flowing fluid, and maintaining the predetermined concentration.

It is further noted that fluid flow controller 54, processor 56 and sensor 58 together form a closed loop control system. Thus, processor 56 controls the operation of fluid flow controller 54 according to a feedback signal received from sensor 58. This closed loop control system allows fluid marking system 50 to maintain the marker concentration at a constant selected value, regardless of fluctuations in the dynamic properties of the flowing fluid, such as temperature, flow rate, viscosity, density, and the like. Thus, fluid marking system 50 can provide a substantially accurate marker concentration despite fluctuations in the dynamic properties of the flowing fluid.

The inventors found out that fluid marking system 50 is capable to produce, for example, a marker concentration of 3 ppm, with a deviation of 5%. Thus, an adulterated fluid which contains the same marker at greater than 3.15 ppm or less than 2.85 ppm, can be detected as such.

It is further noted that fluid marking system 50 can include additional fluid flow controllers similar to fluid flow controller 54. The inlet of each fluid flow controller is coupled with the marker source and the outlet of each fluid flow controller is coupled to a marker injection point, similar to marker injection point 66. Each of the fluid flow controllers is in turn coupled with the processor. In this case, one or more of the fluid flow controllers operate at any given time. Thus, if one of the fluid flow controllers malfunctions and ceases to operate, another fluid flow controller operates.

Fluid type information of the fluid flowing through conduit 64 may be entered into processor 56 or retrieved from a designated fluid type sensor (such as a viscometer), preferably mounted upstream of injection point 66' to provide early indication of a change in fluid type.

In case fluid flow controller 54 is a valve, the processor directs the valve to open for a selected period of time, during which a selected amount of the marker flows from the marker source to the marker injection point. The marker flows through the valve, either under gravity or by a pressure built up by a pump. Marker source 52 can be pressurized, in which case the marker flows to marker injection point 66, through fluid flow controller 54 under a positive pressure.

In case the marker is in form of a fluid (i.e., gas or liquid), the marker source is a pressurized vessel, the fluid flow controller is a valve and the valve opens for a selected period of time, according to a signal received from the processor. Alternatively, the fluid marker can be at atmospheric pressure in which case the fluid flow controller is an aspirator, wherein the aspirator includes a variable orifice and the variable orifice is coupled with the processor. The end of the aspirator is located at a region of the conduit whose cross section is smaller than the adjacent regions, thereby creating a venturi effect. Thus, the flowing fluid sucks the marker at the venturi and the size of the orifice varies according to a signal received from the processor.

Further alternatively, the marker can be in form of a powder which is sucked into the flowing fluid, by venturi effect. Alternatively, the marker can be in form of a miscible solid body which is in contact with the flowing fluid at all times. As the fluid flows in the conduit, selected amounts of the marker particulates separate from the solid marker body and mix with the flowing fluid. Alternatively, the particles of the solid body gradually dissolve in the flowing fluid. The amount of the marker particulates which mix or dissolve in the flowing fluid, can be controlled for example, by controlling the temperature of the solid marker body. Further alternatively, the marker can be a light absorbing or a light emitting substance that inherently absorbs or emits light (fluoresces) at distinct frequencies in response to its exposure to specific radiation (including X-ray or other frequencies). Further alternatively, the marker (either fluid or gas), can be made of a radioactive material whose radiation can be detected at a later stage of authenticating a fluid.

Figure 2:
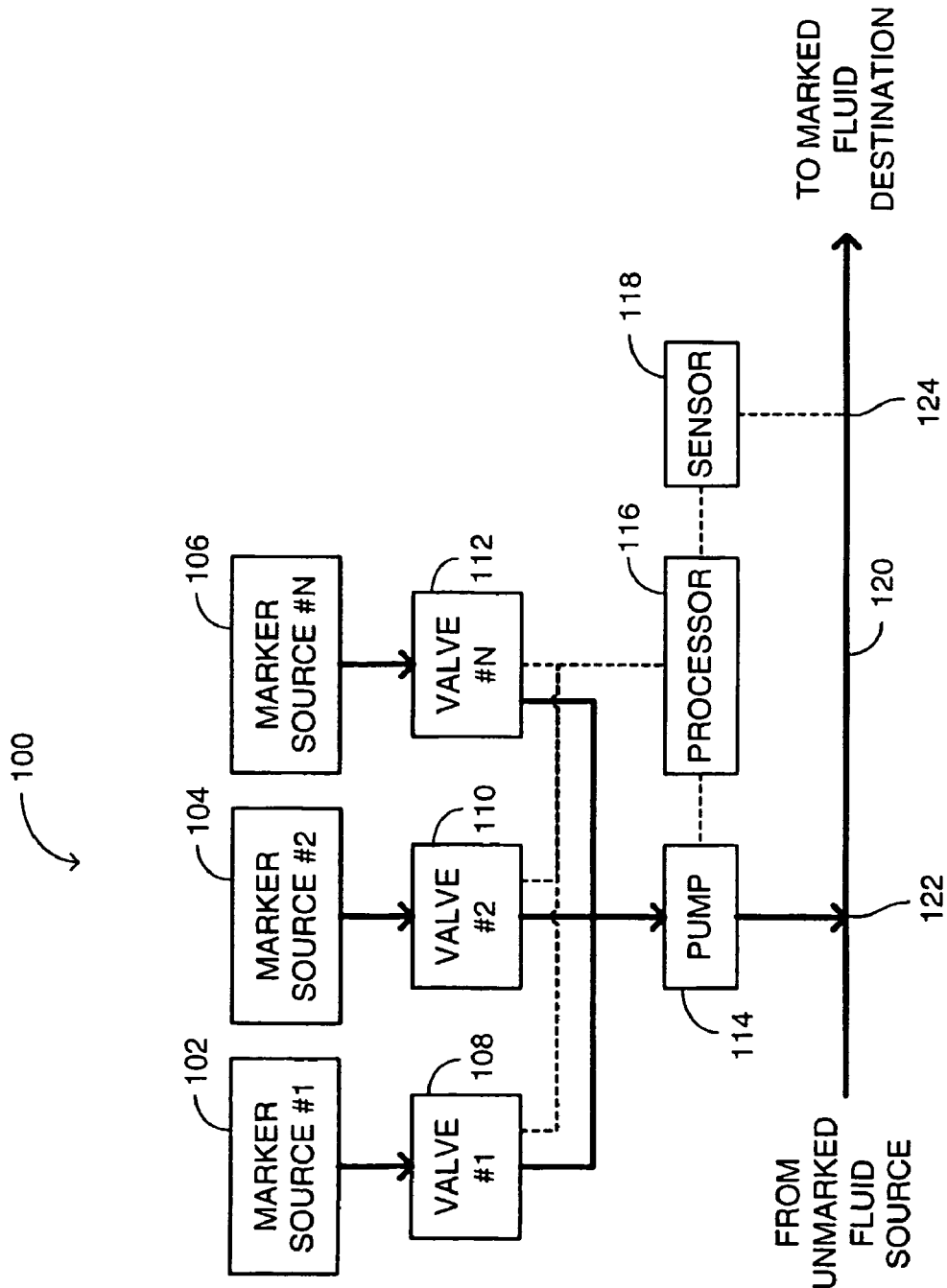
FIG. 2 is a schematic illustration of a fluid marking system, constructed and operative in accordance with another embodiment of the disclosed technique.

Reference is now made to FIG. 2, which is a schematic illustration of a fluid marking system, generally referenced 100, constructed and operative in accordance with another embodiment of the disclosed technique. Fluid marking system 100 includes a plurality of marker sources 102, 104 and 106, a plurality of valves 108, 110 and 112, a pump 114, a processor 116 and a sensor 118. Each of marker sources 102, 104 and 106 is similar to marker source 52 (FIG. 1). The marker in each of marker sources 102, 104 and 106 is similar to the marker as described herein above in connection with FIG. 1. However, the markers in marker sources 102, 104, and 106 are different—either include different marking substances or different concentrations of the same marking substance. Each of valves 108, 110 and 112 is a solenoid operated valve. Pump 114 is similar to the pump as described herein above in connection with FIG. 1. Processor 116 is similar to processor 56 (FIG. 1). Sensor 118 is similar to sensor 58. A fluid flows in a conduit 120 from an unmarked fluid source (not shown) to a marked fluid destination (not shown).

The inlets (not shown) of valves 108, 110 and 112, are coupled with marker sources 102, 104 and 106, respectively. The outlets (not shown) of valves 108, 110 and 112 are coupled with an inlet (not shown) of pump 114. An outlet (not shown) of pump 114 is coupled with a marker injection point 122 of conduit 120. Processor 116 is coupled with valves 108, 110 and 112, pump 114 and with sensor 118.

Sensor 118 measures a property of the fluid which flows in conduit 120, at a measurement point 124 of conduit 120 and provides a signal respective of the measured property, to processor 116. Processor 116 includes information respective of selected ones of marker sources 102, 104 and 106, from which the marker has to be added to the flowing fluid, and thus, the selected ones of valves 108, 110 and 112, respectively, which have to be opened in order to deliver these markers to the flowing fluid. For example, according to this information, only markers from marker sources 102 and 106 have to be added to the flowing fluid, and for this purpose, only valves 108 and 112 have to be opened.

Processor 116 determines the selected amount of each marker and thus, the selected valve opening time for the selected valve, according to the signal received from sensor 118. Processor 116 sequentially provides signals to the selected valves to open and close, and a signal to pump 114 to operate.

For example, processor 116 determines that the marker from marker source 102 has to be pumped for 10 seconds per minute and the marker from marker source 106 has to be pumped for 20 seconds per minute. Processor 116 provides a signal to pump 114 to operate, a signal to valve 108 to open and admit the marker from marker source 102 for 10 seconds and another signal to valve 112 to open and admit the marker from marker source 106 for 20 seconds. Thus, pump 114 injects the marker from marker source 102 to marker injection point 122 for 10 seconds and the marker from marker source 106 for 20 seconds.

In this manner, the fluid which is delivered to the marked fluid destination, is marked with the selected combination of markers, each at the selected marker concentration. Alternatively, processor 116 provides signals to the selected valves to remain open simultaneously.

Figure 3:
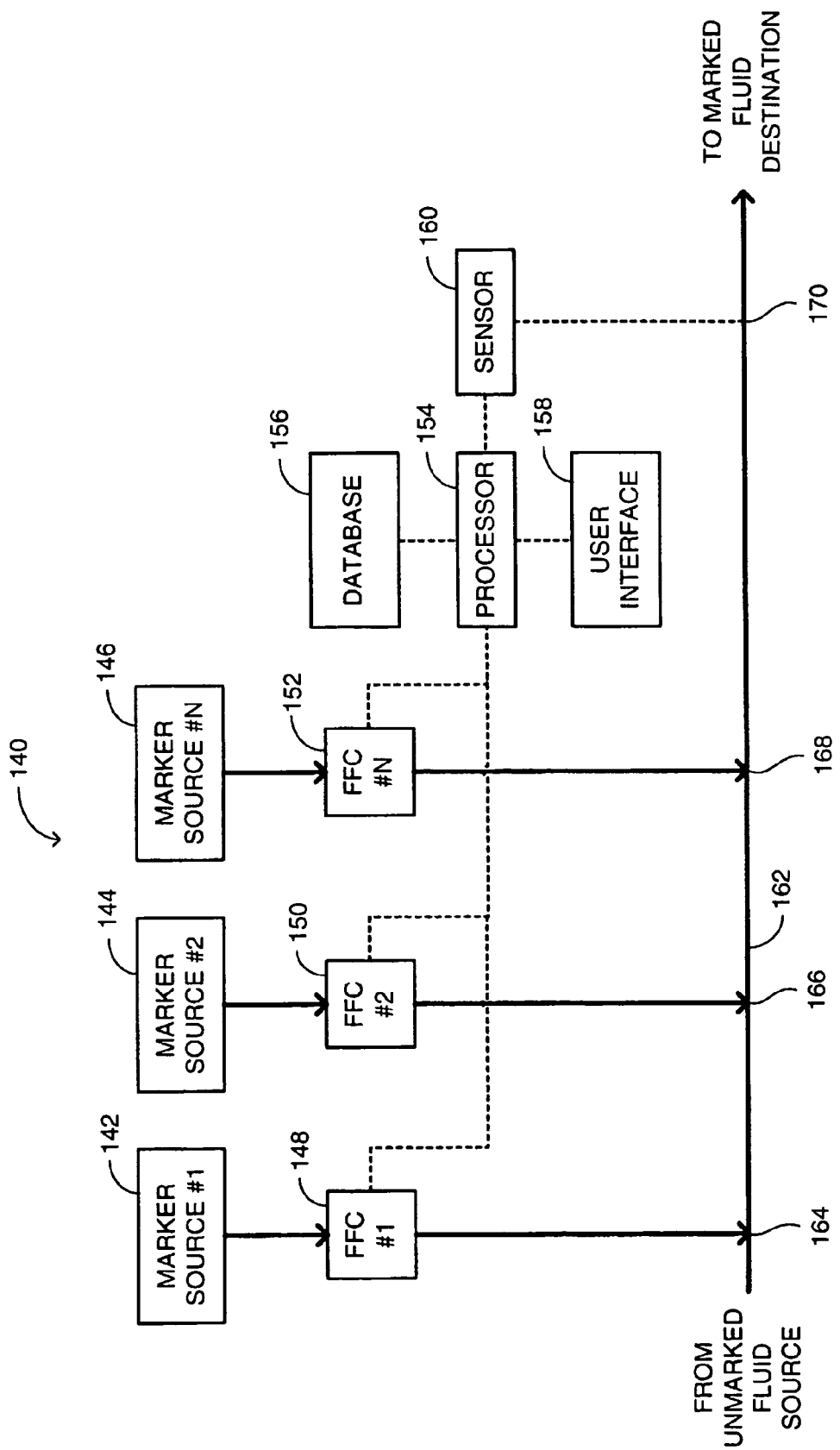
FIG. 3 is a schematic illustration of a fluid marking system, constructed and operative in accordance with a further embodiment of the disclosed technique.

Reference is now made to FIG. 3, which is a schematic illustration of a fluid marking system, generally referenced 140, constructed and operative in accordance with a further embodiment of the disclosed technique. Fluid marking system 140 includes a plurality of marker sources 142, 144 and 146, a plurality of fluid flow controllers (FFC) 148, 150 and 152, a processor 154, a database 156, a user interface 158 and a sensor 160. A fluid flows in a conduit 162 from an unmarked fluid source (not shown) to a marked fluid destination (not shown).

Each of the marker sources 142, 144 and 146 is similar to marker source 52 as described herein above in connection with FIG. 1. Processor 154 is similar to processor 56 (FIG. 1). The marker (not shown) in each of marker sources 142, 144 and 146 is similar to the marker as described herein above in connection with FIG. 1. User interface 158 is a keypad, microphone, speaker, display, touch-screen, warning indicator, and the like, or a combination thereof, through which a user interfaces with processor 154. When fluid marking system 140 malfunctions (e.g., one or more components fail to operate), the warning indicator (not shown) produces an audio or a visual signal, to report the malfunction to the user. Sensor 160 is similar to sensor 58.

Database 156 includes data respective of the operation of each of the fluid flow controllers 148, 150 and 152, data respective of the type of each marker, the molecular structure of each marker, the amount of each marker which is to be added to the flowing fluid, the marker/fluid ratio for each of the markers in the marked fluid destination, the type of sensor 160, a plurality of output signal values of sensor 160, the type of the flowing fluid, the marker key, and the like. Each of fluid flow controllers 148, 150 and 152 is similar to fluid flow controller 54 as described herein above in connection with FIG. 1.

The inlets (not shown) of fluid flow controllers 148, 150 and 152 are coupled with marker sources 142, 144 and 146, respectively. The outlets (not shown) of fluid flow controllers 148, 150 and 152 are coupled with conduit 162 at marker injection points 164, 166 and 168, respectively. Alternatively, fluid flow controllers 148, 150 and 152 may be coupled with conduit 162 at a single marker injection point (not shown). Processor 154 is coupled with fluid flow controllers 148, 150 and 152, database 156, user interface 158, and with sensor 160.

Sensor 160 measures at least one property of the fluid which flows within conduit 162, at a measurement point 170 of conduit 162 and provides a signal respective of this measured property to processor 154. The user enters data respective of the type of the fluid which is to be marked, a marker key, and the like, via user interface 158. The marker key includes information respective of the type of the markers, the molecular structure of each of the markers, a selected combination of these markers, selected marker concentrations for these markers, the time and date of marking, the geographic location of marking, the type and source of the unmarked fluid, and the like. The marker key can be in the form of an alphanumerical code, bar code, and the like.

Processor 154 retrieves marker data from database 156, according to the data received from user interlace 158 and according to the signal received from sensor 160. Database 156 can be replaced by a memory (not shown) within processor 154, in which case processor 154 retrieves the marker data from this memory.

Processor 154 controls the operation of each of the fluid flow controllers 148, 150 and 152, according to the output signal of sensor 160, the data received from user interlace 158 and the marker data retrieved from database 156.

Each of the fluid flow controllers 148, 150 and 152 operates according to a signal received from processor 154 and delivers a selected amount of each marker from each of the marker sources 142, 144 and 146, respectively, to the flowing fluid, at marker injection points 164, 166 and 168, respectively. Thus, when the entire volume of the fluid transfers from the unmarked fluid source to the marked fluid destination, the marked fluid at the marked fluid destination contains each of the markers of marker sources 142, 144 and 146, at the respective marker concentration. Thus, fluid marking system 140 is capable to mark a flowing fluid with different markers at different marker concentrations, thereby allowing a fake fluid to be detected at a greater probability compared to fluid marking system 50.

Figure 4:
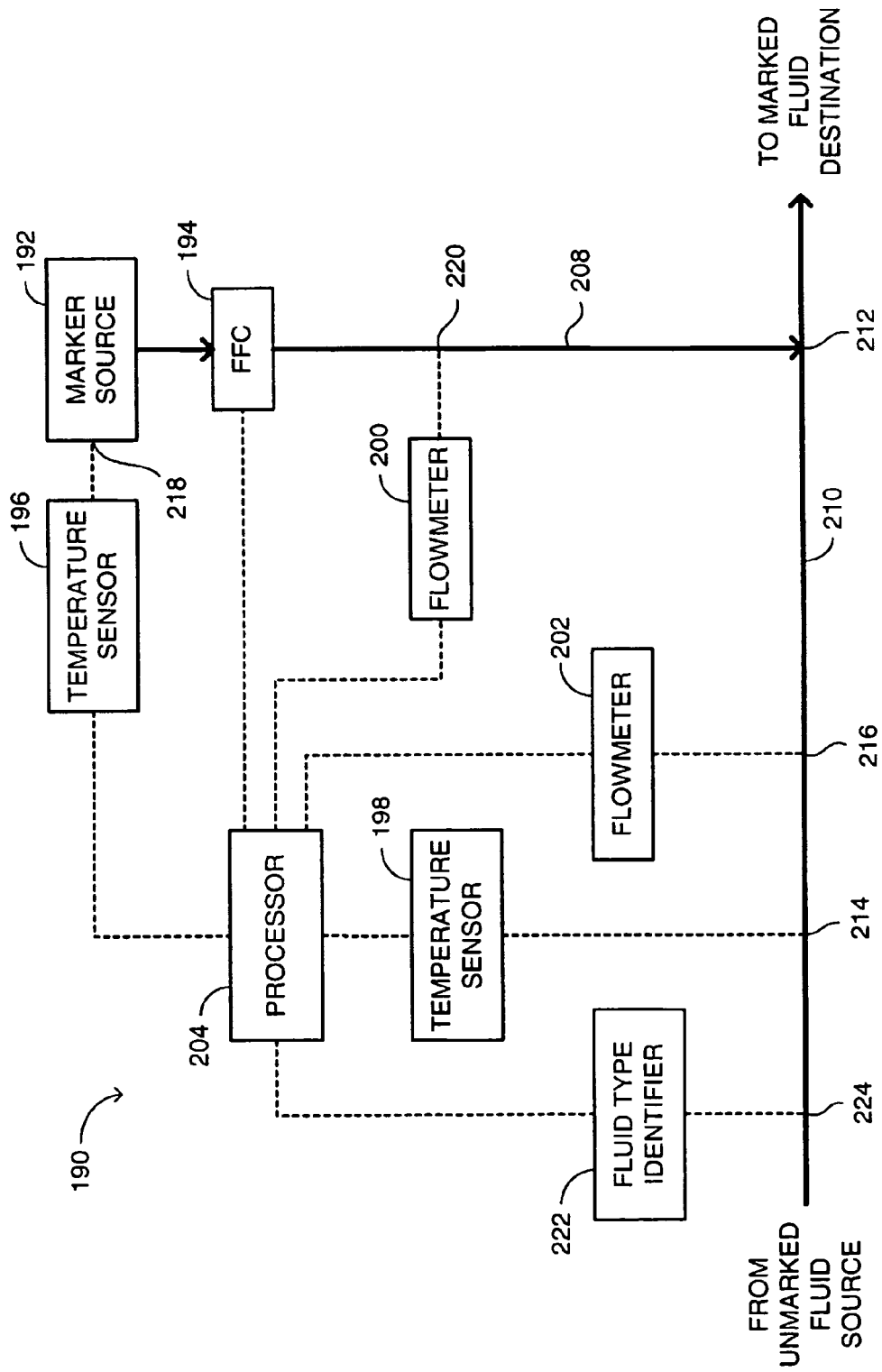
FIG. 4 is a schematic illustration of a fluid marking system, constructed and operative in accordance with another embodiment of the disclosed technique.

Reference is now made to FIG. 4, which is a schematic illustration of a fluid marking system, generally referenced 190, constructed and operative in accordance with another embodiment of the disclosed technique. Fluid marking system 190 includes a marker source 192, a fluid flow controller 194, temperature sensors 196 and 198, flowmeters 200 and 202, a fluid type identifier 222 and a processor 204. Marker source 192 is similar to marker source 52 (FIG. 1) and the marker (not shown) contained within marker source 192 is similar to the marker as described herein above in connection with FIG. 1. Fluid flow controller 194 is similar to fluid flow controller 54 (FIG. 1). Fluid type identifier 222 is a device which identifies the type of a fluid by measuring at least one property of the fluid, such as density, viscosity, dielectric constant, and the like. Thus, for example, fluid type identifier 222 can be a density meter, viscometer, and the like. Processor 204 is similar to processor 56 (FIG. 1).

Processor 204 is coupled with fluid flow controller 194, temperature sensors 196 and 198, fluid type identifier 222 and with flowmeters 200 and 202. A fluid flows within a conduit 210 from an unmarked fluid source (not shown) to a marked fluid destination (not shown). An inlet (not shown) of fluid flow controller 194 is coupled with marker source 192. An outlet (not shown) of fluid flow controller 194 is coupled with conduit 210, at a marker injection point 212 of conduit 210, via a conduit 208. Flowmeter 200 is coupled to conduit 208 at a measurements point 220. Temperature sensor 196 is coupled to marker source 192 at a measurement point 218.

Temperature sensor 198 and flowmeter 202 measure the temperature and the flow rate of the fluid which flows within conduit 210, respectively, at measurement points 214 and 216, respectively, of conduit 210. Fluid type identifier 222 measures a property of the fluid which is flowing in conduit 210, at a measurement point 224 of conduit 210. Flowmeter 200 measures the flow rate of the marker which flows within conduit 208 at measurement point 220. Temperature sensor 196 measures the temperature of the marker which is contained in marker source 192, at measurement point 218. Measurement points 214, 224 and 216 might coincide. Measurement points 214, 224 and 216 are located either downstream of marker injection point 212 or upstream thereof.

"Processor 204 determines the type of the fluid which is flowing within conduit 210, according to a signal received from fluid type identifier 222. Processor 204 controls the operation of fluid flow controller 194 according to signals received from temperature sensors 196 and 198, and flowmeters 200 and 202. Processor 204 controls the operation of fluid flow controller 194, and thus the flow rate of the marker within conduit 208, according to a feedback signal received from flowmeter 200."

The marker concentration required can in some cases be under 10 ppm and even of the order of 1 ppb. The application of accurate amounts of such low concentrations usually requires the dilution of the marker before its addition to the unmarked fluid. The diluter is not necessarily identical with the unmarked fluid, and merely needs to meet certain criteria that allow its addition to the unmarked fluid, such as compatibility with operation and endurance of the unmarked fluid. If the diluted marker is not prepared in advance, the marker, perhaps in varying concentrations, can be diluted on site.

Figure 5:
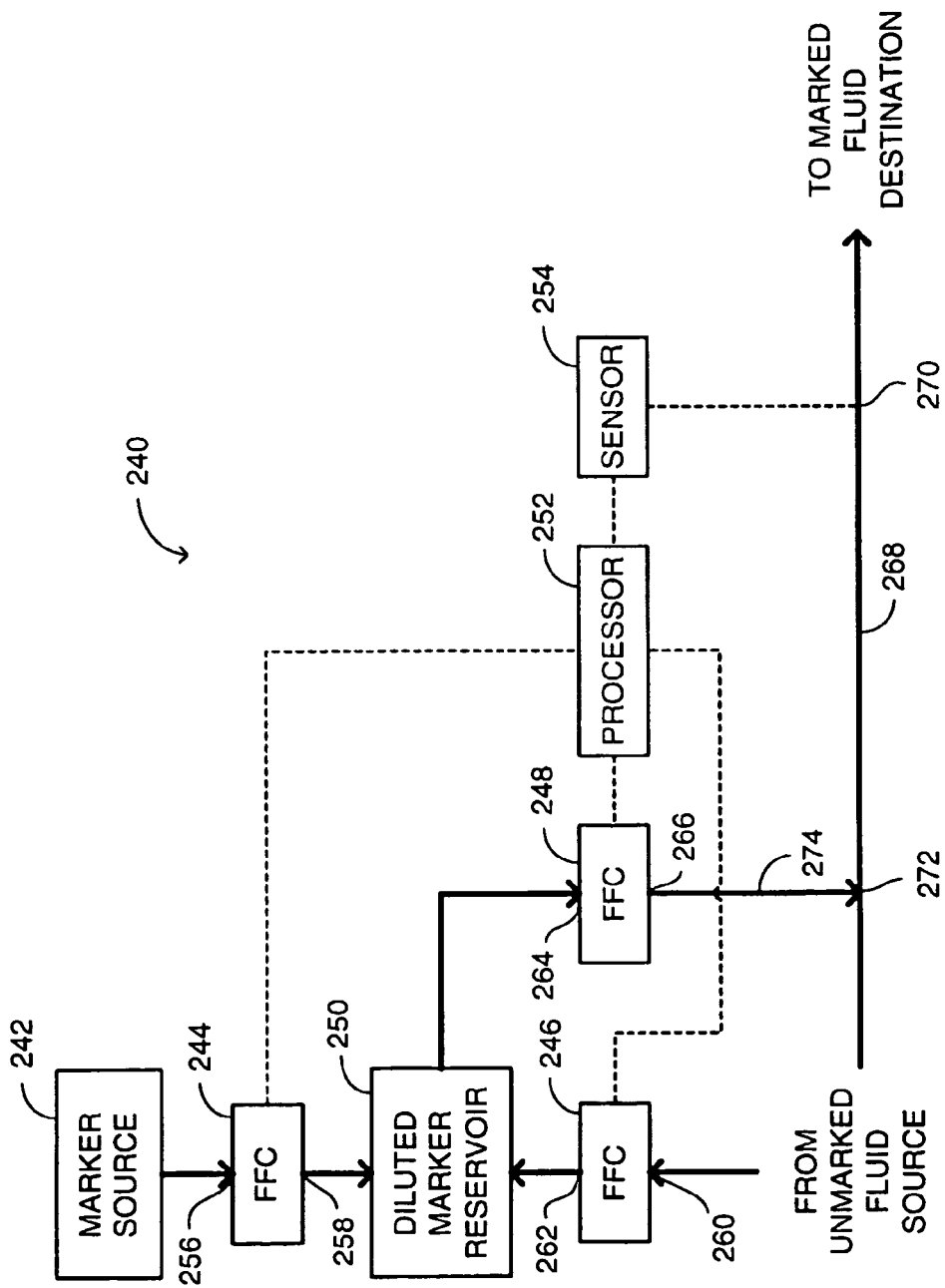
FIG. 5 is a schematic illustration of a fluid marking system, constructed and operative in accordance with a further embodiment of the disclosed technique.

Reference is now made to FIG. 5, which is a schematic illustration of a fluid marking system, generally referenced 240, constructed and operative in accordance with a further embodiment of the disclosed technique. Fluid marking system 240 includes a marker source 242, fluid flow controllers 244, 246 and 248, a diluted marker reservoir 250, a processor 252 and a sensor 254. Fluid flow controller 244 has an inlet 256 and an outlet 258. Fluid flow controller 246 has an inlet 260 and an outlet 262. Fluid flow controller 248 has an inlet 264 and an outlet 266. Each of the fluid flow controllers 244, 246 and 248 is similar to fluid flow controller 54 (FIG. 1). Processor 252 is similar to processor 56 (FIG. 1). Sensor 254 is similar to sensor 58.

Processor 252 is coupled with fluid flow controllers 244, 246 and 248 and with sensor 254. Marker source 242 is coupled with inlet 256. Diluted marker reservoir 250 is coupled with outlets 258 and 262 and with inlet 264.

A fluid flows within a conduit 268, from an unmarked fluid source (not shown) to a marked fluid destination (not shown). Inlet 260 is coupled with the unmarked fluid source. Processor 252 sends a signal to fluid flow controller 246 to admit a selected amount of the fluid from the unmarked fluid source to diluted marker reservoir 250. Processor 252 sends a signal to fluid flow controller 244 to admit a selected amount of marker from marker source 242 to diluted marker reservoir 250. The fluid and the marker mix together in diluted marker reservoir 250 and diluted marker reservoir 250 now contains a diluted marker at a first marker concentration.

Sensor 254 measures a property of the fluid which flows through conduit 268, at a measurement point 270 of conduit 268 and provides a signal respective of the measured property to processor 252. Processor 252 controls the operation of fluid flow controller 248, in order to add a selected amount of the diluted marker from diluted marker reservoir 250, to the fluid which flows within conduit 268. Processor 252 controls the operation of fluid flow controller 248, according to the signal received from sensor 254. Fluid flow controller 248 operates according to a signal received from processor 252, and adds the selected amount of the diluted marker to the fluid which flows in conduit 268, at a marker injection point 272 of conduit 268.

The diluted marker flows from outlet 266 to marker injection point 272 within a conduit 274. The diluted marker which contains marker at the first marker concentration, mixes with the fluid which flows within conduit 268 and thus, the fluid downstream of marker injection point 272 contains marker at a second marker concentration.

It is noted that since the action of fluid flow controller 248 on diluted marker reservoir 250 is multiplicative, the second marker concentration is smaller than the first marker concentration, by several orders of magnitude. For example, if the first marker concentration is equal to 3 ppm and the flow rate in conduit 274 is one thousandths of that in conduit 268, then the second marker concentration is equal to 3 ppb (i.e., one thousandths of the first marker concentration). Thus, fluid marking system 240 allows a fluid to be marked at substantially lower marker concentrations than that of fluid marking system 50.

It is further noted that additional sensors similar to sensor 254 can be employed to measure the properties of the fluid or the marker, at different location within fluid marking system 240. These additional sensors can be located between the unmarked fluid source and the diluted marker reservoir, between the marker source and the diluted marker reservoir, between the diluted marker reservoir and the marker injection point, at the marker source, and the like. Each of the additional sensors is coupled to the processor. The properties of the fluid and the marker are measured at these additional locations, and as described herein above in connection with FIG. 3, the first marker concentration and the second marker concentration can be controlled more accurately.

Alternatively, fluid marking system 240 can operate without fluid flow controllers 244 and 246, in which case diluted marker reservoir 250 is filled in advance with a diluter and the marker in the required concentration. This diluter is a fluid which is compatible with the fluid which is flowing within conduit 268. For example, if gasoline is flowing within conduit 268, then either gasoline or diesel fuel can be used to dilute the marker from marker source 242. Further alternatively, fluid flow controller 246 can be a pump, in order to pump the diluter from a diluter reservoir (not shown) or from a flowing diluter conduit, to diluted marker reservoir 250.

Alternatively, a plurality of different markers are diluted by a diluter in the diluted marker reservoir. The markers can be diluted either manually or automatically. If the markers are diluted automatically, then a plurality of marker sources (not shown) are coupled with an inlet of a marker pump (not shown), through a plurality of valves (not shown), similar to valve 108 of FIG. 2. The inlet of each of the valves is coupled with the respective marker source, the outlet of the valves are coupled with the inlet of the marker pump and the outlet of the marker pump is coupled with the diluted marker reservoir. Each of the valves and the marker pump is coupled with the processor.

Further alternatively, the inlet of fluid flow controller 248 can be coupled with a different diluted marker reservoir at any given time. Alternatively, fluid flow controller 248 is a pump and the inlet of the pump is coupled with a plurality of diluted marker reservoirs, through a plurality of valves similar to valve 108 (FIG. 2), dedicated to each diluted marker reservoir.

Figure 6:
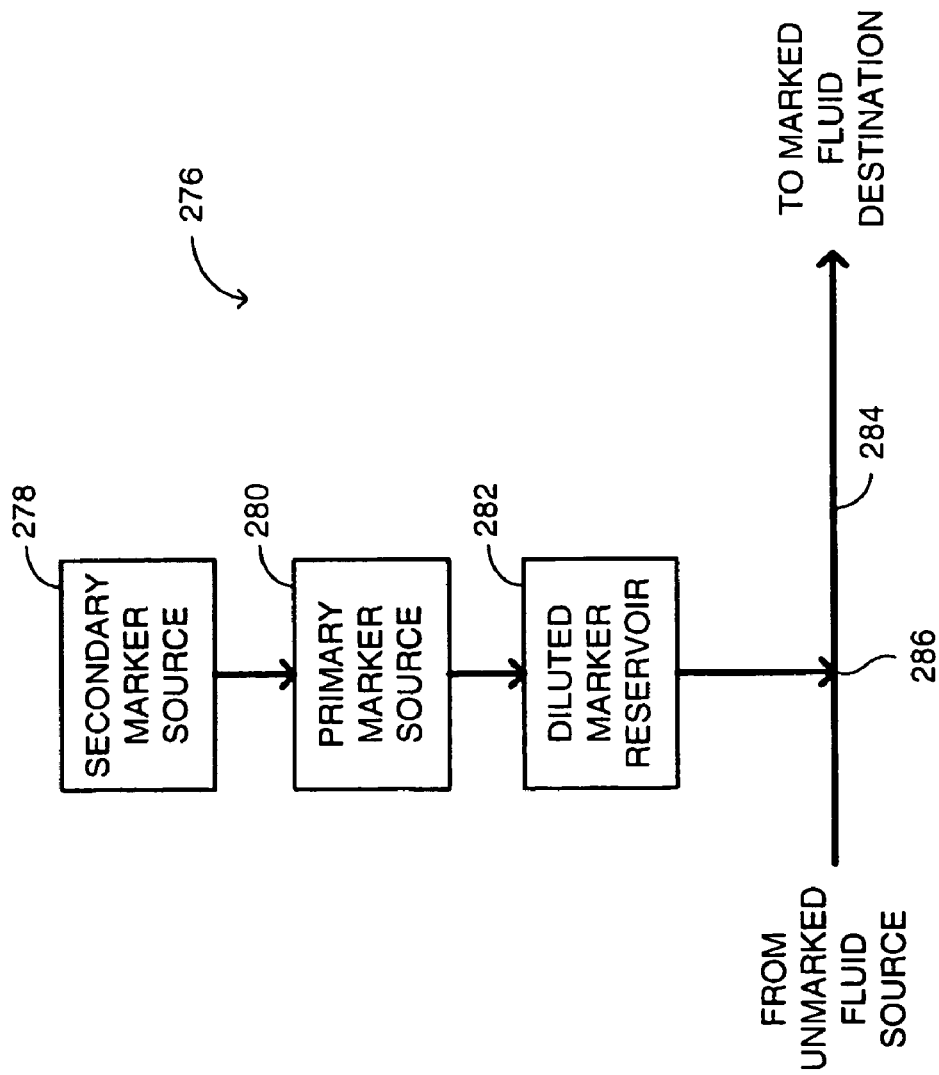
FIG. 6 is a schematic illustration of a fluid marking system, constructed and operative in accordance with another embodiment of the disclosed technique.

Reference is now made to FIG. 6, which is a schematic illustration of a fluid marking system, generally referenced 276, constructed and operative in accordance with another embodiment of the disclosed technique. Fluid marking system 276 includes a secondary marker source 278, a primary marker source 280 and a diluted marker reservoir 282. A fluid flows within a conduit 284 from an unmarked fluid source (not shown), to a marked fluid destination (not shown). Primary marker source 280 is coupled with secondary marker source 278 and with diluted marker reservoir 282. Diluted marker reservoir 282 is coupled with conduit 284 at a marker injection point 286 of conduit 284.

Secondary marker source 278 contains a secondary marker and primary marker source 280 contains a primary marker. Each of the secondary and the primary markers is similar to the marker as described herein above in connection with FIG. 1. Diluted marker reservoir 282 contains a diluter similar to the one described herein above in connection with FIG. 5. Secondary marker source 278 can contain different types of secondary markers and primary marker source 280 can contain different types of primary markers.

The molecular structure of the secondary marker and the primary marker are different. The difference, for example, can be in the atomic elements of the different markers, allowing the distinctive identification of each marker, by a marker detector. The secondary marker is diluted in the primary marker. Thus, the primary marker in primary marker source 280 contains the secondary marker in a substantially low concentration. The contents of primary marker source 280 (i.e., the secondary marker diluted in the primary marker), is further diluted in the diluter of diluted marker reservoir 282. The concentration of the primary marker in the marker solution of diluted marker reservoir 282, is designated by $C_{1P}$ and the concentration of the secondary marker in the marker solution of diluted marker reservoir 282, is designated by $C_{1S}$, where $$C_{1S} \ll C_{1P} \quad (1)$$

The marker solution of diluted marker reservoir 282 is added to the fluid flowing within conduit 284, at marker injection point 286. The marker solution dissolves in the fluid at the marked fluid destination at a concentration $C_{MS}$. The concentration of the primary marker in the marked fluid destination, is designated by $C_{2P}$ and the concentration of the secondary marker in the marked fluid destination, is designated by $C_{2S}$, where $$C_{2P} = C_{MS} \bullet C_{1P} \quad (2)$$

and $$C_{2S} = C_{MS} \bullet C_{1S} \quad (3)$$

thus, $$C_{2P} < C_{1P} \quad (4)$$

$$C_{2S} < C_{1S} \quad (5)$$

and $$C_{2S} \ll C_{2P} \quad (6)$$

"The concentration of the secondary marker in the marked fluid destination, $C_{2S}$ is so low that a marker detector similar to marker detector 302 (FIG. 6), is usually incapable to detect the presence of the secondary marker in the marked fluid destination. However, the presence of the secondary marker in the marked fluid destination, can be detected by more accurate, more time consuming and elaborate methods and detection systems, such method may include increasing the concentration of the secondary marker in the fluid under test. Thus, the amount the secondary marker is selected to be substantially lower than the amount of the primary marker, whereby the presence of the secondary marker in the fluid, is undetectable (e.g., by X-ray fluorescence analyzer detection) without increasing the concentration of the secondary marker in the fluid. Such configuration enhances the security against easy identification of the markers by rogue activities aimed at imitating the marker for falsely reproducing it and adding it to a fake fluid."

It is noted that at such low concentrations the detection of the mere presence of the secondary marker is possible, but usually it is not possible to determine the concentration of the secondary marker in the marked fluid.

Thus, the secondary marker serves as a fingerprint for the primary marker. If a fluid under test is a fake fluid, contains a marker identical with the original primary marker at the correct marker concentration and does not contain the fingerprint (i.e., secondary marker), fluid testing system 300 (FIG. 6) might still determine that the fluid under test is authentic. However, a more elaborate non-conventional detection system (not shown) will detect the absence of the secondary marker in the fluid under test and thus determine that the fluid under test is not authentic.

The marker key as described herein above in connection with FIG. 3, can additionally include information respective of the secondary marker. The marker solution can be prepared either manually or automatically, by employing a combination of a plurality of valves (not shown) and pumps (not shown), coupled with the secondary marker source, the primary marker source and with the diluted marker reservoir.

It is noted that primary marker source 280 can contain a plurality of different secondary markers, wherein it is more difficult for an adulterated fluid to pass a non-conventional fluid test. It is further noted that fluid marking system 276 can include a plurality of secondary marker sources similar to secondary marker source 278, a plurality of primary marker sources similar to primary marker source 280 and a plurality of diluted marker sources similar to diluted marker source 282.

For example, a secondary marker (e.g., ethyliodide) and a primary marker (e.g., tetrabromoethane) are diluted in the marker solution of diluted marker reservoir 282, such that $C_{1P}$ is 2% and $C_{1S}$ is 300 ppm. When the marker solution is added to the fluid flowing in conduit 284, the concentration of the primary marker in the marked fluid destination, $C_{2P}$ is 3 ppm, and the concentration of the secondary marker in the marked fluid destination, $C_{2S}$ is 1 ppb. A fluid testing system similar to fluid testing system 300 (FIG. 6), can detect the presence of the primary marker and measure the marker concentration thereof in the marked fluid, but usually can not detect the presence of the secondary marker in the marked fluid. However, a more accurate fluid testing system can detect the presence of the secondary marker in the marked fluid.

For example, if a fake fluid contains tetrabromoethane at 3.1 ppm and no ethyliodide, then a first fluid testing system similar to fluid testing system 300 (FIG. 6) usually determines that the fake fluid is authentic. However, if the same fake fluid is tested by a more accurate fluid testing system, then this latter fluid testing system determines that no ethyliodide molecules are present in the fake fluid and that the fake fluid is not authentic. Thus, by marking a fluid by fluid marking system 276, the accuracy of determining the authenticity of fluids is higher, compared to a fluid which is marked by fluid marking system 50 (FIG. 1).

Figure 7:
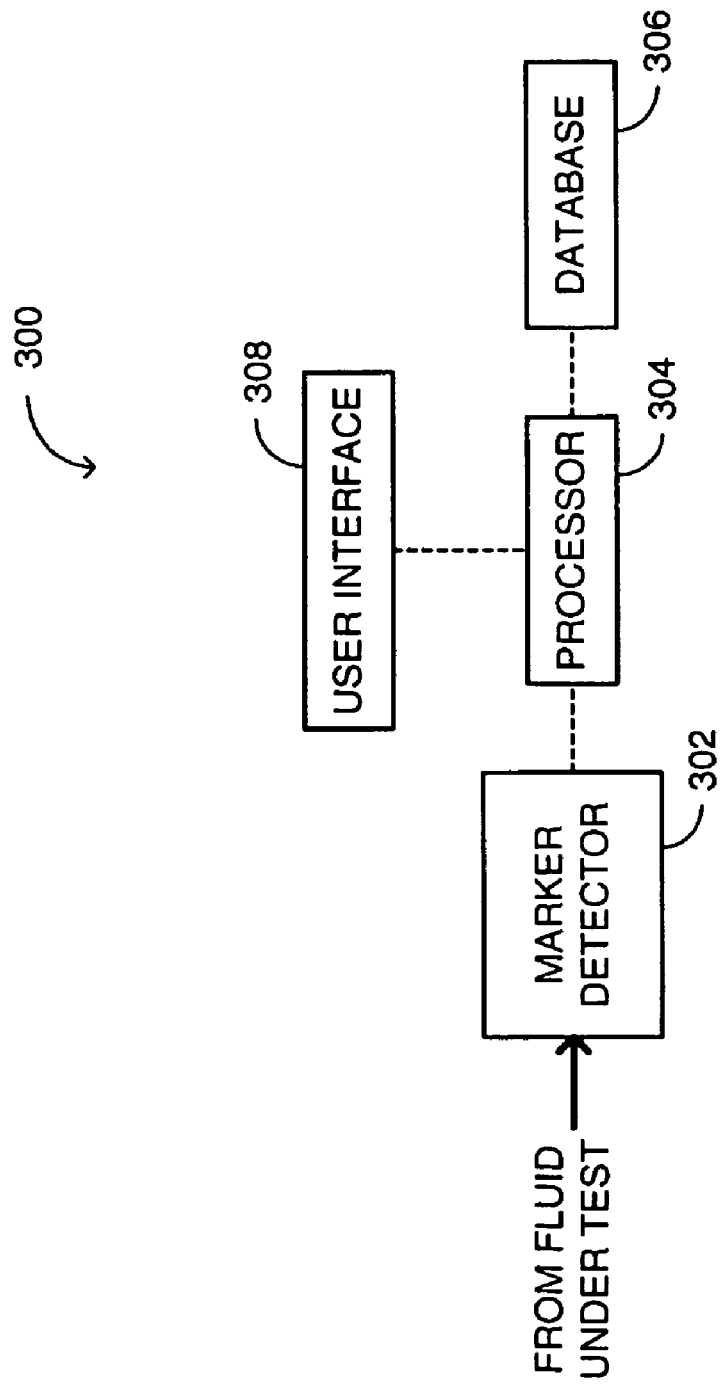
FIG. 7 is a schematic illustration of a fluid testing system, constructed and operative in accordance with a further embodiment of the disclosed technique.

Reference is now made to FIG. 7, which is a schematic illustration of a fluid testing system, generally referenced 300, constructed and operative in accordance with a further embodiment of the disclosed technique. Fluid testing system 300 includes a marker detector 302, a processor 304, a database 306 and a user interface 308.

Marker detector 302 is a device which can detect the presence, the absence and the type of a marker in a fluid and measure the properties of this marker in the fluid. Marker detector 302 can measure at least one property of the marker, such as radiation level, absorbed or emitted light wavelength, atomic energy level, frequency of atomic vibrations, and the like.

Thus, marker detector 302 can be a spectrometer, X-ray fluorescence (XRF) analyzer, gas chromatograph, optical detector, radiation detector, nuclear magnetic resonance (NMR), and the like. User interface 308 is similar to user interface 158 (FIG. 2). Processor 304 is similar to processor 56 (FIG. 1). Database 306 includes data respective of different marker keys (i.e., marker data).

Processor 304 is coupled with marker detector 302, database 306 and with user interface 308. The user enters a marker key via user interface 308 and user interface 308 provides the data respective of the marker key, to processor 304. This marker key is similar to the one described herein above in connection with FIG. 2. Processor 304 provides a signal to marker detector 302 to detect the presence, the absence and the type of the marker in the fluid and measure the properties of the marker in the fluid. Marker detector 302 can either test the bulk of the fluid (e.g., oil flowing in a pipeline) or a sample of the fluid which is taken from the bulk fluid (e.g., a sample of fuel taken from a gas tank). Marker detector 302 tests the fluid and provides data respective of the outcome of the test, to processor 304. Processor 304 retrieves marker data from database 306, according to the data received from user interface 308. Database 306 can be replaced by a memory (not shown) within processor 304, in which case processor 304 retrieves the marker data from this memory.

Marker detector 302 identifies the presence of a marker in the fluid and measures the marker concentration in this fluid. Processor 304 retrieves marker data respective of the identity of the marker and the preselected marker concentration, from database 306, according to the marker key. Processor 304 compares the marker detector data with the marker data. If the marker type information included in the marker detector data and in the marker data, match and the marker concentration indicated by the marker detector data equals, within the acceptable error range, to the marker concentration indicated by the marker data, then processor 304 determines that the fluid under test is authentic.

If the marker type information included in the marker detector data and in the marker data, do not match, or the marker concentration indicated by the marker detector data deviates, beyond the acceptable error range, from the marker concentration indicated by the marker data, then processor 304 determines that the fluid under test is not authentic. Processor 304 provides a signal respective of the authenticity of the fluid under test to user interface 308 and user interface 308 produces an output according to the signal received from processor 304.

For example, the marker key includes information respective of the refinery which is the source of a fluid. Processor 304 processes the marker detector data received from marker detector 302 and the marker data retrieved from database 306 and determines whether the source of the fluid under test matches the information of the marker key respective of fluid originating from the refinery.

Alternatively, processor 304 includes marker data respective of a single marker key and fluid testing system 300 is devoid of database 306. Processor 304 compares the marker detector data received from marker detector 302 with the marker data stored in processor 304 and determines whether the fluid under test is authentic or not. A fluid testing system similar to fluid testing system 300, can be installed for example, in an automobile in order to determine whether the gas tank of the automobile is being filled with a predetermined grade of a fuel.

Figure 8:
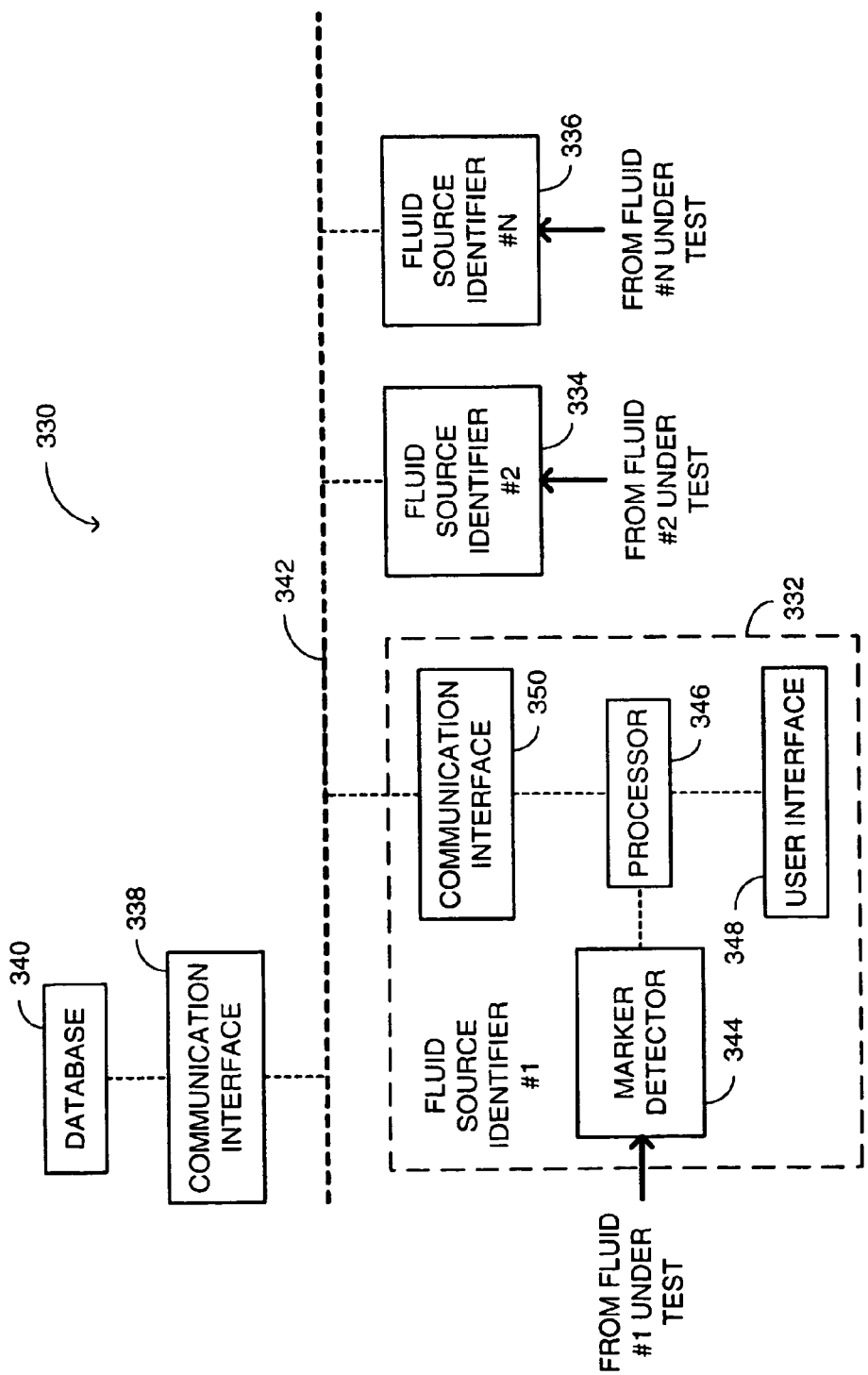
FIG. 8 is a schematic illustration of a fluid testing system, constructed and operative in accordance with another embodiment of the disclosed technique.

Reference is now made to FIG. 8, which is a schematic illustration of a fluid testing system, generally referenced 330, constructed and operative in accordance with another embodiment of the disclosed technique. Fluid testing fluid testing system 330 includes a plurality of fluid source identifiers 332, 334 and 336, a communication interface 338, a database 340 and a bus 342. Communication interface 338 is coupled with database 340 and with bus 342. Fluid source identifiers 332, 334 and 336 are coupled with bus 342.

Bus 342 is either a radio link (e.g., through a satellite, cellular network, free-space optics (FSO), and the like), a line connection or a combination thereof. Each of fluid source identifiers 332, 334 and 336 and communication interface 338 can be coupled with bus 342 either by a radio link, a line connection or a combination thereof.

Fluid source identifier 332 includes a marker detector 344, a processor 346, a user interface 348 and a communication interface 350. Marker detector 344 and user interface 348 are similar to marker detector 302 (FIG. 5) and user interface 308, respectively. Database 340 is similar to database 306 (FIG. 5). Processor 346 is similar to processor 56 (FIG. 1). Processor 346 is coupled with marker detector 344, user interface 348 and with communication interface 350. Communication interface 350 is coupled with bus 342.

The description of fluid source identifier 332 below, applies also to fluid source identifiers 334 and 336. The user enters data respective of the type of fluid #1, a marker key, and the like, via user interface 348 and user interface 348 provides this data to processor 346. Processor 346 provides a signal to marker detector 344 to test fluid #1. Marker detector 344 performs the test on fluid #1 and provides data respective of the outcome of the test, to processor 346.

Processor 346 establishes a link with database 340, via communication interfaces 350 and 338 and bus 342 and retrieves data from database 340, according to the data received from user interface 348. Processor 346 processes the data received from marker detector 344, the data received from user interface 348 and the data retrieved from database 340, determines whether fluid #1 is authentic or not and provides a respective signal to user interface 348. User interface 348 provides an output according to the signal received from processor 346. It is noted that since no database is included in fluid source identifiers 332, 334 and 336, each of fluid source identifiers 332, 334 and 336 can be portable and compact, thereby facilitating onsite authentication of fluids. Fluid testing system 330 can be employed, for example, for monitoring the fuels at different gas stations, the different storage tanks in each gas station, the distribution sites of a petroleum incorporation, and so forth.

Figure 9:
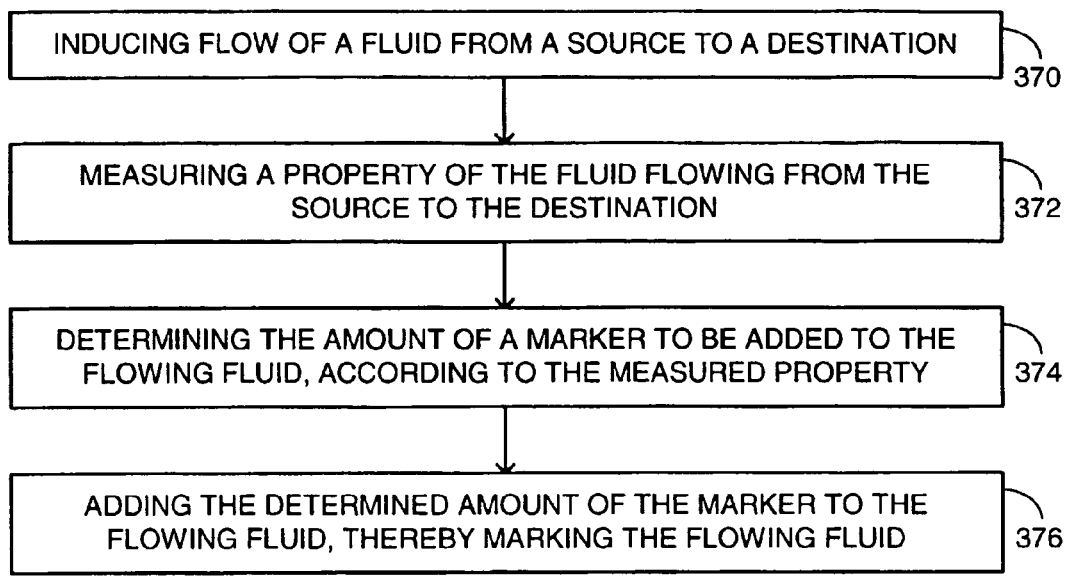
FIG. 9 is a schematic illustration of a method for marking a fluid, operative in accordance with a further embodiment of the disclosed technique.

Reference is now made to FIG. 9, which is a schematic illustration of a method for marking a fluid, operative in accordance with a further embodiment of the disclosed technique. In procedure 370, a fluid is induced to flow from an unmarked fluid source to a marked fluid destination. With reference to FIG. 1, a fluid flows in conduit 64, from an unmarked fluid source to a marked fluid destination, either by the action of a pump or under gravity.

In procedure 372, a property of the fluid which flows from the unmarked fluid source to the marked fluid destination, is measured. With reference to FIG. 1, sensor 58 measures the flow rate of the fluid which flows within conduit 64 and provides a flow rate signal, to processor 56.

In procedure 374, the amount of a marker which is to be added to the flowing fluid is determined, according to the measured property. With reference to FIG. 1, processor 56 determines the amount of the marker which is to be added to the fluid at marker injection point 66, according to the flow rate signal and by employing a look-up table stored in processor 56. For example, if fluid flow controller 54 is a variable displacement pump, then processor 56 determines a pumping rate for fluid flow controller 54.

In procedure 376, the determined amount of the marker is added to the flowing fluid, thereby marking the flowing fluid. With reference to FIG. 1, processor 56 provides a signal to fluid flow controller 54 to control the operation of fluid flow controller 54, such that fluid flow controller 54 admits the determined amount of the marker to the flowing fluid. For example, if fluid flow controller 54 is a variable displacement pump, then fluid flow controller 54 operates at the determined pumping rate, in order to inject the determined amount of the marker at marker injection point 66, within a given period of time.

Figure 10:
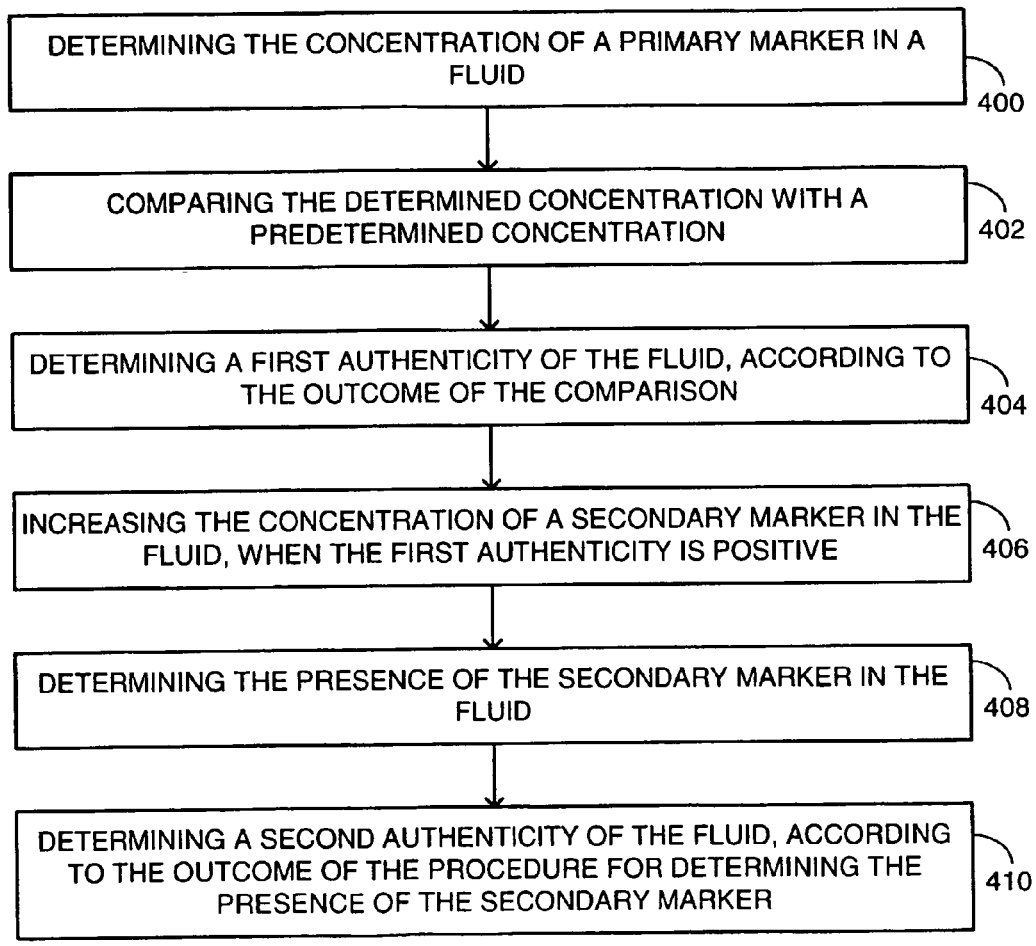
FIG. 10 is a schematic illustration of a method for testing a fluid, operative in accordance with another embodiment of the disclosed technique.

Reference is now made to FIG. 10, which is a schematic illustration of a method for testing a fluid, operative in accordance with another embodiment of the disclosed technique. In procedure 400, the concentration of a primary marker in a fluid, is determined. With reference to FIG. 7, marker detector 302 determines the concentration of a primary marker in a fluid under test. This primary marker may have been added to the fluid under test, by a fluid marking system similar to fluid marking system 276 (FIG. 6). It is noted that fluid marking system 276 can add a plurality of different primary markers and thus, marker detector 302 determines the concentration of a plurality of different primary markers.

In procedure 402, the determined concentration is compared with a predetermined concentration. With reference to FIG. 7, processor 304 receives marker detector data from marker detector 302, wherein this marker detector data includes information respective of the concentration of the primary marker in the fluid under test. Processor 304 retrieves marker data from database 306 according to the marker key data which the user entered to user interface 308. Processor 304 compares the determined concentration included in the marker detector data, with the predetermined marker concentration included in the marker data.

In procedure 404, a first authenticity of the fluid is determined, according to the outcome of the comparison. With reference to FIG. 6, if the determined concentration equals, within an acceptable range, to the predetermined concentration, then processor 304 determines that the fluid under test is authentic. If the fluid is determined to be authentic, then the method proceeds to procedure 406. Since procedure 406 is relatively expensive and time consuming, it is performed only in case the outcome of procedure 404 is dubious. If it is determined that the fluid is not authentic, then the method ceases at procedure 404.

In procedure 408, the presence of the secondary marker in the fluid is determined. The secondary marker may have been added to the fluid, by a fluid marking system similar to fluid marking system 276 (FIG. 6). The presence of the secondary marker in the fluid under test is determined by methods such as those described herein above in connection with FIG. 6 (procedure 410). It is noted that fluid marking system 276 can add a plurality of different secondary markers to a fluid, and thus, in procedure 408 the presence of a plurality of different secondary markers is determined.

It will be appreciated by persons skilled in the art that the disclosed technique is not limited to what has been particularly shown and described hereinabove. Rather the scope of the disclosed technique is defined only by the claims, which follow.

The invention claimed is:

1. System for marking, detecting and authenticating a hydrocarbon fluid, the system comprising:
   a hydrocarbon fluid source;
   a hydrocarbon fluid destination;
   a flow line between the hydrocarbon fluid source and the hydrocarbon fluid destination;
   at least one primary marker source containing at least one primary marker;
   at least one secondary marker source containing at least one secondary marker detectable by X-ray fluorescence, which is different from said at least one primary marker;
   wherein said secondary marker is selected from the list consisting of:
   a chemical compound having the general formula $C_n H_{2n+2-m} X_m$, where $n=1, 2, 3 \ldots$, $m=1, 2, 3 \ldots$;
   a chemical compound having the general formula $C_2(H_{2n+1-m}C_n)_4 X_m$ where $n=1, 2, 3 \ldots$, $m=1, 2, 3 \ldots$;
   a chemical compound having the general formula $C_{n-m}H_{2n+2}Y_m$, where $n=1, 2, 3 \ldots$, $m=1, 2, 3 \ldots$, $m<n$; and
   a chemical compound having the formula $C_2(H_{2n+1}C_{n-m})_4 Y_m$, where $n=1, 2, 3 \ldots$, $m=1, 2, 3 \ldots$,
   where "X" and "Y" designate a chemical element which can be detected by an X-ray fluorescence analyzer;
   at least one sensor configured to continuously determine at least a flow rate of the hydrocarbon fluid;
   a first detection system for determining a concentration of said at least one primary marker in said hydrocarbon fluid;
   a second detection system for detecting at least the presence of said at least one secondary marker in said hydrocarbon fluid, wherein the second detection system is X-ray fluorescence;
   at least one first fluid flow controller coupled with said at least one primary marker source for dispensing a determined amount of said at least one primary marker into the flow line and at least one second fluid flow controller coupled with said at least one secondary marker source for dispensing a determined amount of said at least one secondary marker into the flow line with the at least one primary marker, and
   a processor coupled with said first detection system and with said at least one first and second fluid flow controllers, said processor being preprogrammed to determine said amounts of the at least one primary and at least one secondary markers according to said flow rate and predetermined concentrations of said at least one primary and said at least one secondary markers in said hydrocarbon fluid at said hydrocarbon fluid destination, and further configured to direct said at least one first and second fluid flow controllers to dispense said determined amounts of said at least one primary and at least one secondary markers into said hydrocarbon fluid to mark and maintain said hydrocarbon fluid at said predetermined concentrations to enable a determination of the authenticity of said hydrocarbon fluid, wherein said predetermined concentrations are selected such that said predetermined concentration of said at least one secondary marker in said hydrocarbon fluid is substantially lower than said predetermined concentration of said at least one primary marker in said hydrocarbon fluid, and is undetectable by said first detection system and detectable by said second X-ray fluorescence detection system.

2. The system according to claim 1, wherein said at least one fluid flow controller is selected from the list consisting of:
pump; and
valve.

3. The system according to claim 2, wherein the type of said pump is selected from the list consisting of:
constant displacement; and
variable displacement.

4. The system according to claim 1, wherein said at least one sensor determining the flow rate is located downstream of marker injection points, at which said at least one first and at least one second fluid flow controllers dispense said predetermined amounts of said at least one primary marker and at least one secondary marker to said fluid.

5. The system according to claim 1, wherein said at least one sensor is a flowmeter.

6. The system according to claim 1, wherein said predetermined concentration of said at least one primary marker equals, within an acceptable range, to 3 parts per million.

7. The system according to claim 1, wherein the deviation of said predetermined concentration approximately equals to 5% of the value of said predetermined concentration.

8. The system according to claim 1, further comprising:
a user interface coupled with said processor,
wherein said user interface receives a marker key from a user, and
wherein said processor determines said amount according to said marker key.

9. The system according to claim 8, wherein said marker key includes said predetermined concentration.

10. The system according to claim 8, wherein the type of said marker key is selected from the list consisting of:
alphanumeric code; and
bar code.

11. The system according to claim 1, further comprising a database associated with said processor, said database comprising data respective of said predetermined concentration, wherein said processor determines said amount by employing said data.

12. The system according to claim 1, further comprising a fluid type identifier coupled to said processor,
wherein said fluid type identifier determines the type of said fluid according to its physical-chemical property, and
wherein said processor determines said amount according to said type.

13. The system according to claim 12, wherein said physical-chemical property is selected from the list consisting of density, viscosity, and dielectric constant.

14. The system according to claim 1, wherein said at least one sensor is a flowmeter.

15. The system according to claim 1, wherein "X" is a halogen selected from the list consisting of:
fluorine;
chlorine;
bromine;
iodine; and
lithium.

16. The system according to claim 1, wherein "Y" is selected from the list consisting of:
silicon; and
germanium.

17. The system according to claim 1, wherein the type of said at least one primary marker and said at least one secondary marker is selected from the listy consisting of:
liquid;
gas; and
solid.

18. The system according to claim 1, wherein said hydrocarbon fluid is selected from the list consisting of:
naphtha;
gasoline;
diesel fuel;
jet fuel;
kerosene;
propane;
crude oil;
lubricant;
hydraulic fluid; and
natural gas.

19. The system according to claim 1, further comprising a temperature sensor.

* * * * *